(12) United States Patent
Lagrange

(10) Patent No.: US 7,326,259 B2
(45) Date of Patent: Feb. 5, 2008

(54) USE OF POLYCATIONIC COMPOUNDS IN THE DYEING OF KERATINOUS FIBRES

(75) Inventor: Alain Lagrange, Coupvray (FR)

(73) Assignee: L'Oreal S.A., Paris (FR)

(*) Notice: Subject to any disclaimer, the term of this patent is extended or adjusted under 35 U.S.C. 154(b) by 280 days.

(21) Appl. No.: 11/158,329

(22) Filed: Jun. 22, 2005

(65) Prior Publication Data

US 2006/0037151 A1 Feb. 23, 2006

Related U.S. Application Data

(60) Provisional application No. 60/616,434, filed on Oct. 7, 2004.

(30) Foreign Application Priority Data

Jun. 23, 2004 (FR) .................. 04 06848

(51) Int. Cl.
*A61K 7/13* (2006.01)

(52) U.S. Cl. .............. 8/405; 8/406; 8/407; 8/565; 8/567; 8/568; 8/570; 8/571; 8/572; 8/573; 8/574; 8/654; 548/146; 548/300

(58) Field of Classification Search ........... 8/405, 8/406, 407, 565, 567, 568, 570, 571, 572, 8/573, 574, 654; 548/146, 300
See application file for complete search history.

(56) References Cited

U.S. PATENT DOCUMENTS

| | | | |
|---|---|---|---|
| 3,536,436 | A | 10/1970 | Lange |
| 3,578,386 | A | 5/1971 | Kalopissis et al. |
| 3,649,162 | A | 3/1972 | James |
| 4,003,699 | A | 1/1977 | Rose et al. |
| RE30,199 | E | 1/1980 | Rose et al. |
| 4,823,985 | A | 4/1989 | Grollier et al. |
| 5,061,289 | A | 10/1991 | Clausen et al. |
| 5,380,340 | A | 1/1995 | Neunhoeffer et al. |
| 5,534,267 | A | 7/1996 | Neunhoeffer et al. |
| 5,708,151 | A | 1/1998 | Möckli |
| 5,766,576 | A | 6/1998 | Löwe et al. |
| 6,099,592 | A | 8/2000 | Vidal et al. |
| 6,284,003 | B1 | 9/2001 | Rose et al. |
| 6,730,789 | B1 | 5/2004 | Birault et al. |
| 2003/0177591 | A1 | 9/2003 | Möckli |
| 2004/0093676 | A1* | 5/2004 | Vidal et al. ............ 8/405 |

FOREIGN PATENT DOCUMENTS

| | | |
|---|---|---|
| DE | 23 59 399 | 6/1975 |
| DE | 38 43 892 | 6/1990 |
| DE | 41 28 490 | 3/1993 |
| DE | 41 33 957 | 4/1993 |
| DE | 195 43 988 | 5/1997 |
| EP | 0 714 954 | 6/1996 |
| EP | 0 770 375 | 5/1997 |
| FR | 2 434 190 | 3/1980 |
| FR | 2 586 913 | 3/1987 |
| FR | 2 733 749 | 11/1996 |
| FR | 2 801 308 | 5/2001 |
| GB | 1 026 978 | 4/1966 |
| GB | 1 153 196 | 5/1969 |
| GB | 2 028 856 | 3/1980 |
| JP | 88-169 571 | 7/1988 |
| JP | 2-19576 | 1/1990 |
| JP | 2526099 | 5/1996 |
| WO | WO 94/08969 | 4/1994 |
| WO | WO 94/08970 | 4/1994 |
| WO | WO 95/01772 | 1/1995 |
| WO | WO 95/15144 | 6/1995 |
| WO | WO 96/15765 | 5/1996 |

OTHER PUBLICATIONS

STIC Search Report dated May 10, 2007.*
French Search Report for FR 04 06848 (French Priority Application for U.S. Appl. No. 11/158,329, the present application) dated Feb. 2, 2005.
English language Derwent Abstract for DE 41 28 490.
English language Derwent Abstract for EP 0 770 375.
English language Derwent Abstract for FR 2 434 190.
English language Derwent Abstract for JP 2-19576 and JP 2526099.
English language Derwent Abstract for DE 41 28 490 (1993).
English language Derwent Abstract for EP 0 770 375 (1997).
English language Derwent Abstract for FR 2 434 190 (1980).
English language Derwent Abstract for JP 2-19576 and JP 2526099 (1990) & (1996).

* cited by examiner

*Primary Examiner*—Eisa Elhilo
(74) *Attorney, Agent, or Firm*—Finnegan, Henderson, Farabow, Garrett & Dunner L.L.P.

(57) ABSTRACT

A subject-matter of the present patent application is the use, as direct dye in dyeing compositions for keratinous fibres, in particular human keratinous fibres, such as the hair, or for the manufacture of such compositions, of a specific polycationic compound.

28 Claims, No Drawings

USE OF POLYCATIONIC COMPOUNDS IN THE DYEING OF KERATINOUS FIBRES

This application claims priority to French Application No. FR 04/06848, filed on Jun. 23, 2004, and U.S. Provisional Application No. 60/616,434, filed on Oct. 7, 2004, the contents of both of which are herein incorporated by reference.

A subject-matter of the present patent application is the use of specific polycationic compounds as direct dyes in dyeing compositions for the dyeing of keratinous fibres and in particular human hair. The present application is also targeted at dyeing compositions based on these dyes and at the use of these compositions in the dyeing of keratinous fibres.

It is known to dye keratinous fibres and in particular human hair with dyeing compositions comprising oxidation dye precursors, generally referred to as oxidation bases, such as ortho- or para-phenylenediamines, ortho- or para-aminophenols and heterocyclic compounds. These oxidation bases are colourless or weakly coloured compounds which, in combination with oxidizing products, can give rise, by an oxidative coupling process, to coloured compounds. These dyes, which are insoluble in the dyeing medium, are trapped within the individual hair.

It is also known that it is possible to vary the shades obtained with these oxidation bases by combining them with couplers or colouring modifiers, the latter being chosen in particular from aromatic meta-diamines, meta-aminophenols, meta-diphenols and certain heterocyclic compounds, such as indole compounds.

The variety of the molecules involved as oxidation bases and couplers makes it possible to obtain a rich palette of colours.

The "permanent" colouring obtained by virtue of these oxidation dyes has, however, to satisfy a certain number of requirements. Thus, it must be without disadvantage toxicologically and it must make it possible to obtain shades with the desired intensity and behave well in the face of external agents, such as light, bad weather, washing, permanent waving operations, perspiration and rubbing.

The dyes must also make it possible to cover white hair and, finally, be as non-selective as possible, that is to say make it possible to obtain the smallest possible differences in colouring along the same keratinous fibre, which is generally sensitized (i.e. damaged) to varying extents between its tip and its root.

It is also known to dye keratinous fibres with a direct or semipermanent colouring. The process conventionally used in direct colouring consists in applying direct dyes to keratinous fibres, direct dyes being coloured and colouring molecules which have an affinity for the fibres, in leaving to stand in order to allow the coloured molecules to penetrate, by diffusion, inside the individual hair, and then in rinsing the fibres.

In contrast to oxidation dyeing compositions, the direct or semipermanent dyeing compositions can be employed without the presence of an oxidizing agent. These dyeing operations can be carried out repeatedly without damaging the keratinous fibre.

It is known, for example, to use nitrobenzene, anthraquinone, nitropyridine, azo, xanthene, acridine, azine, or triarylmethane direct dyes.

This results in particularly chromatic colourings which, however, are temporary or semipermanent because of the nature of the bonds between the direct dyes and the keratinous fibre. These interactions mean that the desorption of the dyes from the surface and/or from the core of the fibre easily occurs. The colourings generally exhibit a low dyeing power and poor resistance to washing operations or to perspiration. In addition, these direct dyes are generally sensitive to light as the resistance of the chromophore with regard to photochemical attacks is low, which results in dulling of the colouring of the hair over time. The sensitivity of these dyes to light depends on their uniform or nonuniform distribution in and/or over the keratinous fibre.

Furthermore, conventional direct dyes are not always completely harmless; for this reason, in hair cosmetics, there is a search for colouring molecules of this type which are more effective still in terms of harmlessness.

There exists a real need to have available direct dyeing compositions which are improved in terms of resistance to shampooing operations and of absorption of the dye.

Surprisingly and advantageously, the Applicant Company has just discovered that the use of specific polycationic compounds in compositions for the dyeing of keratinous fibres, in particular human keratinous fibres, such as the hair, makes it possible to obtain dyeing compositions which exhibit these improvements.

In addition to their advantage in terms of harmlessness, the compositions-according to the present patent application make it possible to obtain colourings which are resistant to external agents (such as the sun or bad weather), as well as to shampooing operations and to perspiration, and make it possible to obtain intense and long-lasting shades on the fibres.

A subject-matter of the present invention is thus the use, as direct dye in dyeing compositions for keratinous fibres, in particular human keratinous fibres, such as the hair, or for the manufacture of such compositions, of compounds of formula (I) described below.

Another subject-matter of the invention is a dyeing composition for the dyeing of keratinous fibres, in particular human keratinous fibres, such as the hair, comprising, in an appropriate dyeing medium, at least one oxidation base and at least one compound of formula (I).

Another subject-matter of the invention relates to a process for the dyeing of keratinous fibres, in particular human keratinous fibres, such as the hair, which employs this composition.

Another subject-matter of the invention is the use of the composition of the present invention on keratinous fibres, in particular human keratinous fibres, such as the hair, in order to obtain colourings exhibiting good resistance to external agents and to shampooing operations. The tautomeric forms of the compounds of formula (I) can also be used.

Other characteristics, aspects, subject-matters and advantages of the invention will become even more clearly apparent on reading the description and examples which follow.

The compounds which can be used as direct dyes according to the invention correspond to the formula (I):

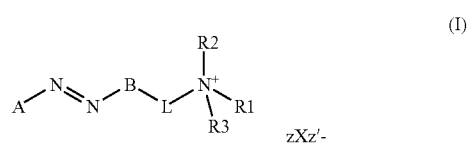

in which:

$X^{z'-}$ denotes an organic or inorganic anion;

z and z' are such that the overall charge of the molecule is zero;

A denotes a heterocyclic ring carrying a positive charge which has the following meaning: substituted or unsubstituted thiazolium, the substituents of the thiazolium comprising in total at most one alkoxycarbonyl functional group; substituted or unsubstituted imidazolium; substituted or unsubstituted benzimidazolium; substituted or unsubstituted benzothiazolium pyridino; substituted or unsubstituted naphthothiazolium and substituted benzothiazolium;

B denotes an optionally substituted $C_6$-$C_{30}$ arylene group or an optionally substituted 5- to 10-membered heterocyclic group;

L denotes a substituted or unsubstituted, linear, branched or cyclic, alkylene chain comprising from 1 to 30 carbon atoms, it being possible for the chain to be or not to be interrupted or terminated by one or more heteroatomic groups chosen from O, S, NH or NR, with R representing a linear or branched $C_1$-$C_{10}$ alkyl radical, or interrupted by one or more heterocyclic or nonheterocyclic, aromatic or non-aromatic, cyclic radicals, it being possible for the chain itself to carry one or more quaternary cationic charges and it being possible for one or more carbon atoms of the chain to be replaced by a carbonyl group; preferably, L comprises at least one —$CH_2$— group;

R1, R2 and R3 denote, independently of one another, an optionally substituted, linear, branched or cyclic, $C_1$-$C_{10}$ alkyl radical; an optionally substituted, linear or branched, $C_1$-$C_{10}$ arylalkyl radical; an optionally substituted aryl radical; or a linear or branched $C_1$-$C_{10}$ aryloxyalkyl radical; the said aryl groups preferably being $C_6$ aryl groups; it being possible for at least one of the R1, R2 and R3 radicals to form, with the nitrogen atom carrying it (them) and optionally with L, an optionally substituted, saturated or unsaturated, 5- to 10-membered heterocycle which can comprise one or more additional heteroatoms.

According to one alternative form, two of the R1, R2 and R3 radicals form a ring with the nitrogen atom carrying them and the remaining radical optionally forms a ring with L.

According to another alternative form, one of the R1, R2 or R3 radicals forms a heterocycle with the nitrogen atom carrying it and with L, the remaining two radicals not being involved in a ring with the nitrogen atom carrying them.

Preferably, R1, R2 and/or R3 do not form a ring with L.

The term "substituent" is understood to mean, within the meaning of the present invention, a radical chosen from hydroxyl, amino, halogen, $C_1$-$C_{10}$ alkyl, $C_6$-$C_{30}$ aryl, $C_1$-$C_{10}$ hydroxyalkyl, mono- or di($C_1$-$C_{10}$)alkylamino, mono- or dihydroxy ($C_1$-$C_{10}$)alkylamino, ($C_1$-$C_{10}$)alkoxy, amido, phenylamido, carboxyl, ($C_1$-$C_{10}$)alkoxycarbonyl, sulphonato, ($C_1$-$C_{10}$)alkoxycarbonyl($C_1$-$C_{10}$)alkyl or 5- to 10-membered heterocycle radicals or a heterocycle $C_1$-$C_{10}$ alkyl radical with a heterocycle having from 5 to 10 ring members.

Mention may be made, as arylene group, of the benzene, naphthalene, anthracene and perylene groups.

Mention may be made, as organic or inorganic anions, of halide ions and in particular chloride, bromide or iodide ions, methanesulphonate ions, methyl sulphate ions, bromate or chlorate ions, acetate ions, sulphate ions, tartrate ions, lactate ions, citrate ions or chlorozincate ions.

Mention may be made, as heterocycle suitable for the group B, without implied limitation, of the thiazole, pyridine and pyrimidine rings.

Preferably, B is an arylene group.

Mention may be made, among the compounds of formula (I), of the following compounds:

2-[[4-[ethyl[2-trimethylammonio)ethyl]amino]phenyl]-azo]-4-(methoxycarbonyl)-5-(2-methoxy-2-oxoethyl)-3-methylthiazolium

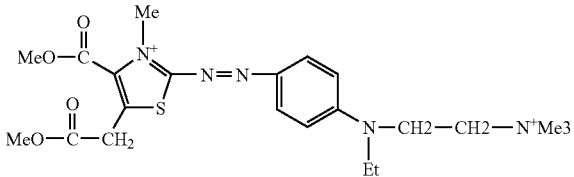

2-[[4-[[2-[dimethyl(phenylmethyl)ammonio]ethyl]ethylamino]phenyl]azo]-3-methylthiazolium dichloride

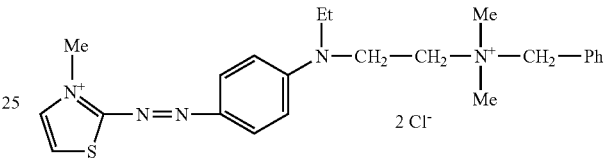

2-[[4-(diethylamino)-2-[[trimethylammonio)acetyl]-amino]phenyl]azo]-5-(ethoxycarbonyl)-3-methyl-4-phenylthiazolium

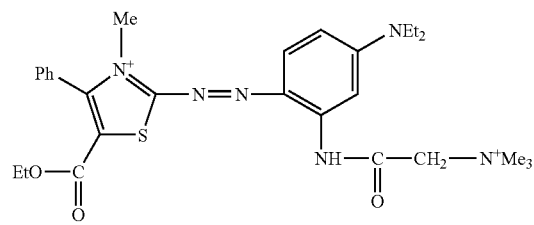

2-[[4-(diethylamino)-2-[[(trimethylammonio)acetyl]oxy]-phenyl]azo]-5-(ethoxycarbonyl)-3,4-dimethylthiazolium bis[tetrafluoroborate(1-)]

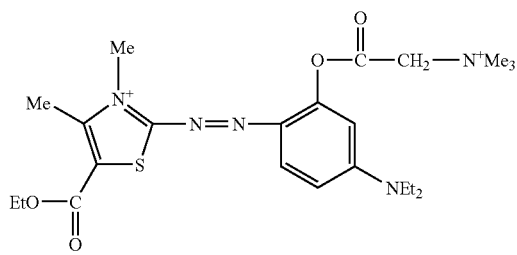

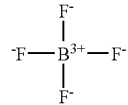

2-[[4-(diethylamino)-2-[[(trimethylammonio)acetyl]oxy]-phenyl]azo]-5-(ethoxycarbonyl)-3,4-dimethylthiazolium

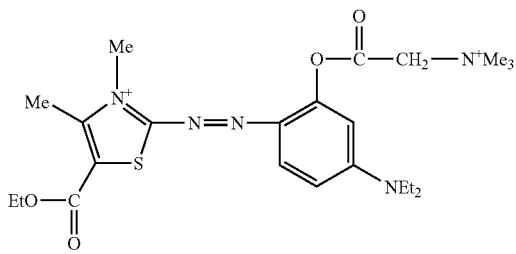

2-[[4-[ethyl[2-[(2-hydroxypropyl)dimethylammonio]-ethyl]amino]-2-methylphenyl]azo]-3-methylthiazolium dichloride

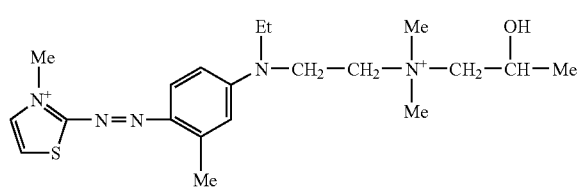

2-[[4-[ethyl[2-(trimethylammonio)ethyl]amino]phenyl]-azo]-3-methylthiazolium dichloride

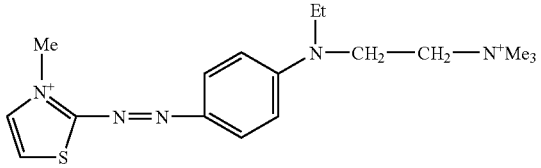

2-[[4-[ethyl[2-(trimethylammonio)ethyl]amino]phenyl]-azo]-3-methyl-4-phenylthiazolium bis[tetrafluoroborate (1-)]

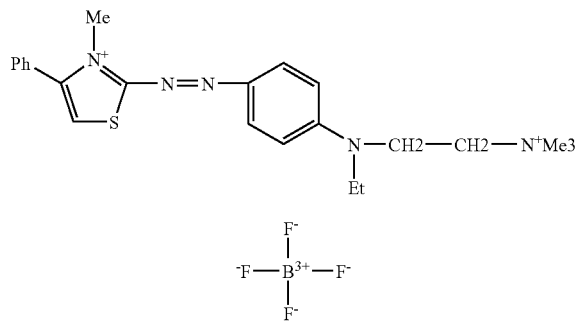

2-[[4-[ethyl[2-(trimethylammonio)ethyl]amino]phenyl]-azo]-3-methyl-4-phenylthiazolium

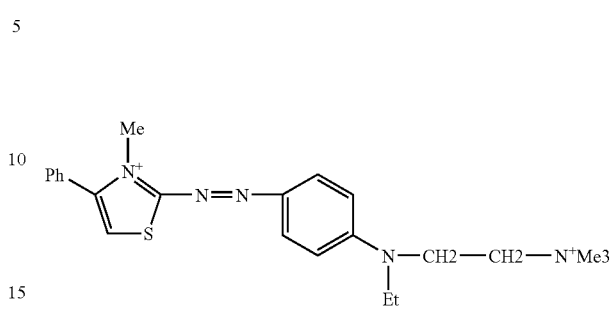

1-(2-{(4-methoxyphenyl)-[3-methyl-4-(thiazol-3-ium-2-ylazo)phenyl]amino}ethyl)-4-methylpyridinium chloride

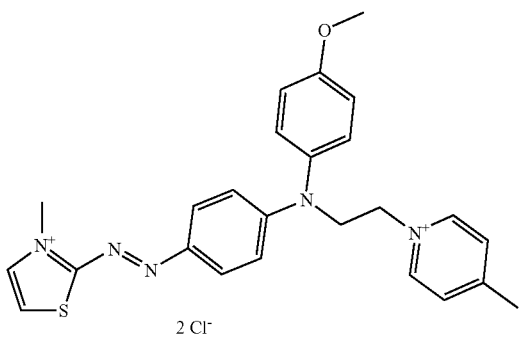

1-(2-{phenyl-[5-ethoxycarbonyl-3,4-dimethyl-4-(thiazol-3-ium-2-ylazo)phenyl]amino}ethyl)pyridinium chlorozincate

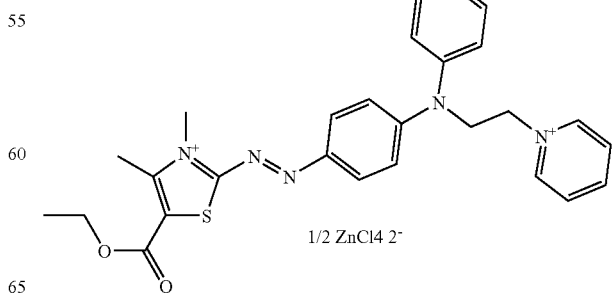

7

1-(2-{(4-methoxyphenyl)[5-ethoxycarbonyl-3,4-dimethyl-4-(thiazol-3-ium-2-ylazo)phenyl]amino}ethyl)-4-methylpyridinium chloride

8

1-(3-{[4-(5-ethoxycarbonyl-3,4-dimethyl-4-(thiazol-3-ium-2-ylazo)phenyl](phenyl)amino}-2-hydroxypropyl)-pyridinium chlorozincate

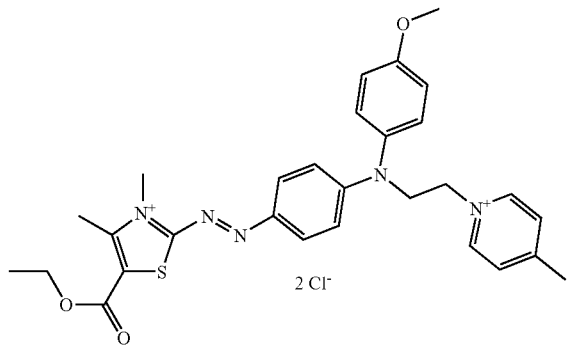

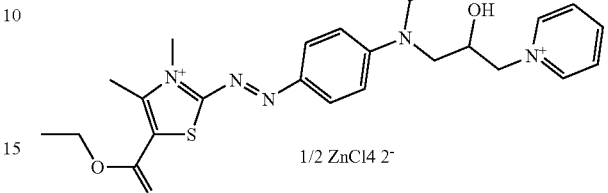

4-dimethylamino-1-(2-{[4-(5-ethoxycarbonyl-3,4-dimethyl-4-(thiazol-3-ium-2-ylazo)phenyl](p-toly)amino}-ethyl)pyridinium chlorozincate 1-{3-[[4-(5-ethoxycarbonyl-3,4-dimethyl-4-(thiazol-3-ium-2-ylazo)phenyl](4-methoxyphenyl)amino]-2-hydroxypropyl}-4-methylpyridinium chloride

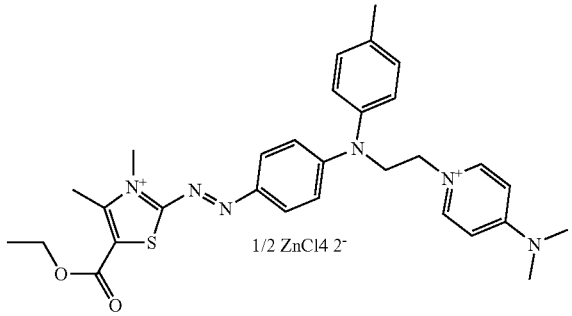

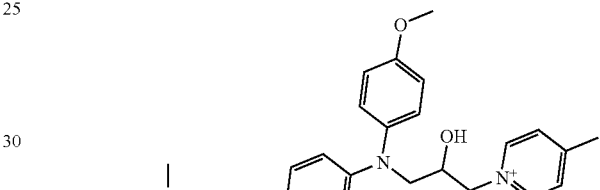

4-[4-[(1,3-dimethyl-1H-imidazolium-2-yl)azo]phenyl]-1,1-dimethylpiperazinium diiodide 1-{2-[[4-(5-acetyl-3,4-dimethyl-4-(thiazol-3-ium-2-ylazo)phenyl](4-methoxyphenyl)amino]ethyl}pyridinium chloride

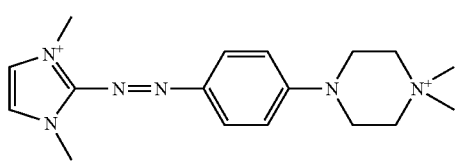

2-[[4-[ethyl[2-[[(trimethylammonio)acetyl]amino]ethyl]-amino]-2-methylphenyl]azo]-1,3-dimethyl-1H-imidazolium diiodide

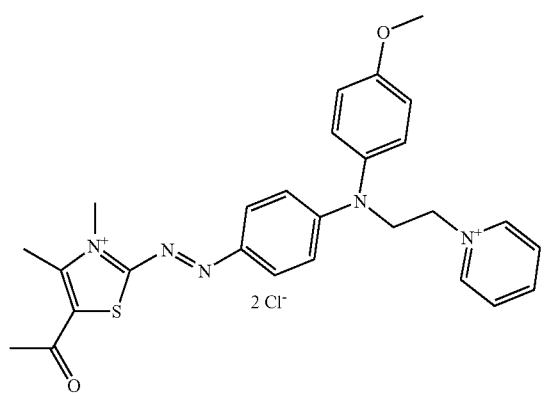

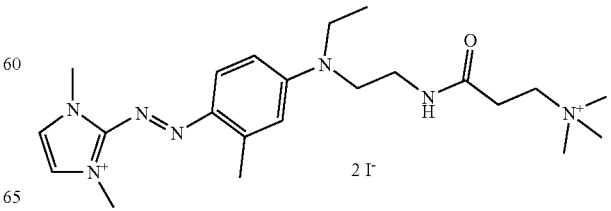

2-[[4-[[3-(diethylmethylammonio)-2-hydroxypropyl]
ethylamino]-2-methylphenyl]azo]-1,3-dimethyl-1H-
imidazolium diiodide 2-[[4-[ethyl[2-(trimethylammonio)ethyl]amino]phe-
nyl]-azo]-3-methylnapththo[2,1-d]thiazolium dichlo-
ride

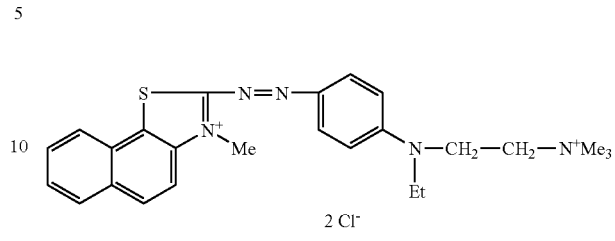

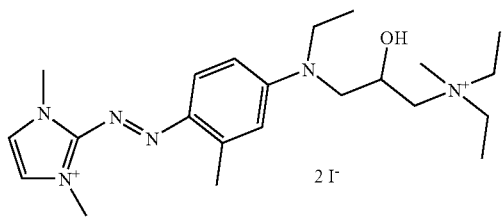

2-[[4-anilino-2-(ethylamino)-6-[[3-(trimethylammo-
nio)-propyl]amino]-5-pyrimidinyl]azo]-6-methoxy-
3-methylbenzothiazolium bis(methylsulphate)

2-[[4-[[2-(diethylmethylammonio)ethyl]ethylamino]-
2-methylphenyl]azo]-1,3-dimethyl-1H-imidazolium
diiodide

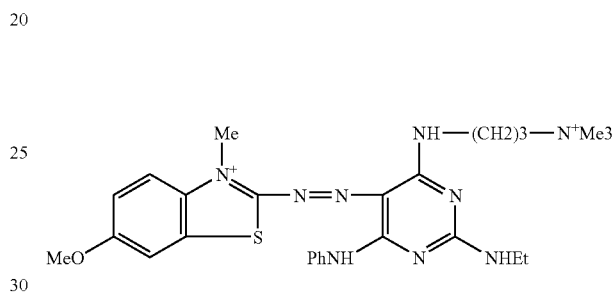

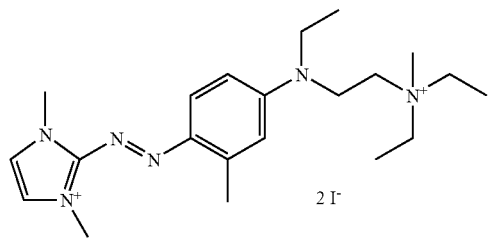

2-[[2-(ethylamino)-4-(phenylamino)-6-[[3-(trimethy-
lammonio)propyl]amino]-5-pyrimidinyl]azo]-6meth-
oxy-3-methylbenzothiazolium 2-[[4-[ethyl[2-(trimethylammonio)ethyl]amino]phe-
nyl]-azo]-1,3-dimethyl-1H-imidazolium diiodide

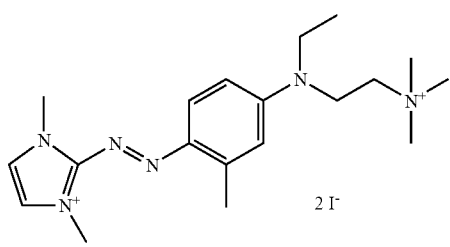

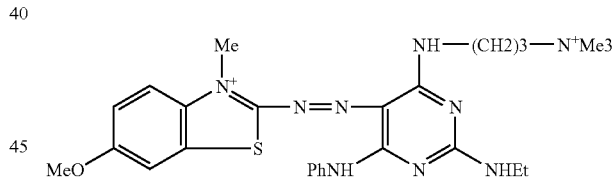

2-[[4-[ethyl[2-(trimethylammonio)ethyl]amino]phe-
nyl]-azo]-6-methoxy-3-methylbenzothiazolium sul-
phate 2-[[4-[[2-(diethylmethylammonio)ethyl]ethylamino]-
phenyl]azo]-1,3-dimethyl-1H-imidazolium diiodide

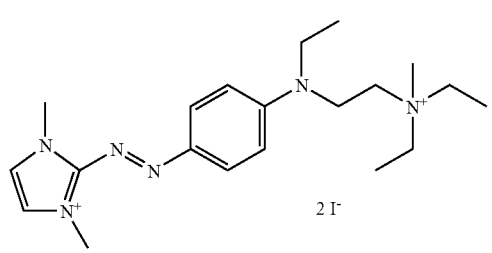

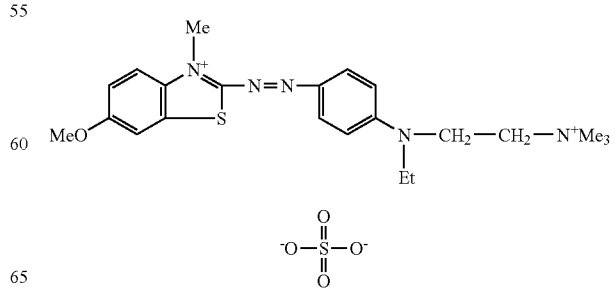

11

2-[[4-[ethyl[2-(trimethylammonio)ethyl]amino]phenyl]-azo]-6-methoxy-3-methylbenzothiazolium diacetate

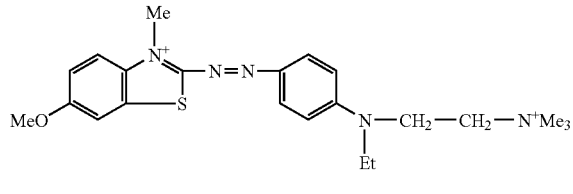

2-[[4-[ethyl[2-(trimethylammonio)ethyl]amino]phenyl]-azo]-6-methoxy-3-methylbenzothiazolium bis(methylsulphate)

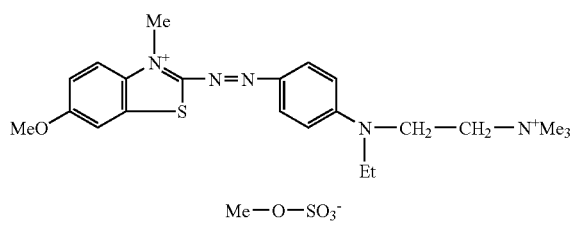

2-[[4-[ethyl[2-(trimethylammonio)ethyl]amino]phenyl]-azo]-6-methoxy-3-methylbenzothiazolium

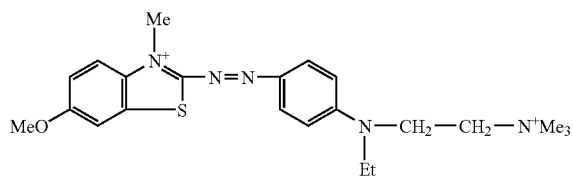

6-ethoxy-2-[[4-[ethyl[2-hydroxy-3-(trimethylammonio)-propyl]amino]-2-methylphenyl]azo]-3-methyl-benzothiazolium bis[tetrafluoroborate(1-)]

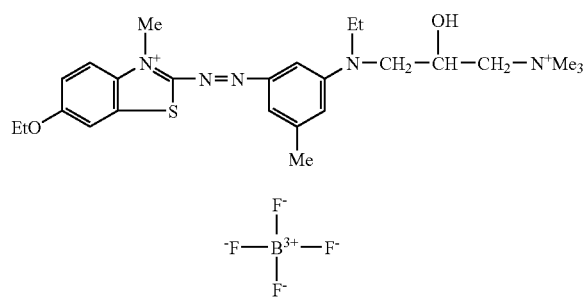

12

6-ethoxy-2-[[4-[ethyl[2-hydroxy-3-(trimethylammonio)-propyl]amino]-2-methylphenyl]azo]-3-methyl-benzothiazolium

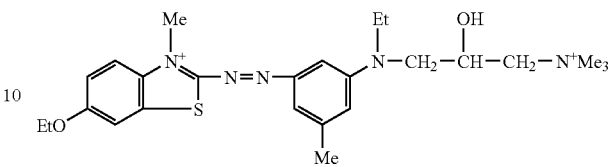

3-[4-(6-methoxy-3-methylbenzothiazol-3-ium)phenyl]-3-aza-6-azoniaspiro[5.5]undecane dichloride

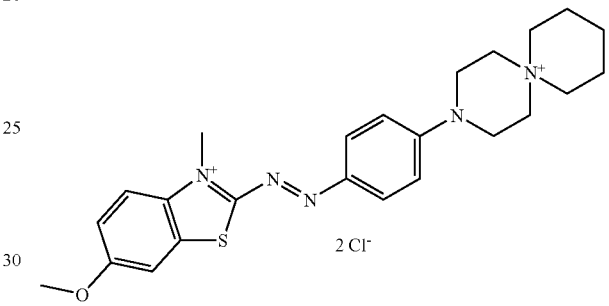

diethyl(2-{ethyl[4-(3-methylbenzothiazol-2-ylazo)phenyl]amino}ethyl)(2-phenoxyethyl)ammonium dichloride

1-(2-{ethyl[4-(6-methoxy-3-methylbenzothiazolium-2-ylazo)phenyl]amino}ethyl)pyridinium tetrafluoroborate

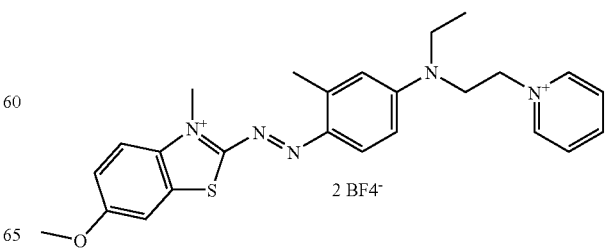

13

(2-{ethyl[4-(1,2,3-trimethyl-1H-benzoimidazolium-5-ylazo)phenyl]amino}ethyl)trimethylammonium chlorozincate

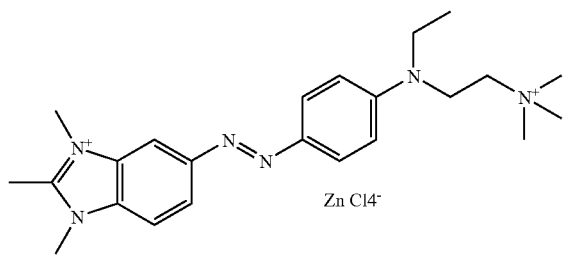

diethylmethyl{2-[3-methyl[4-(1,2,3-trimethyl-1H-benzoimidazolium-5-ylazo)phenylamino]ethyl}ammonium chlorozincate

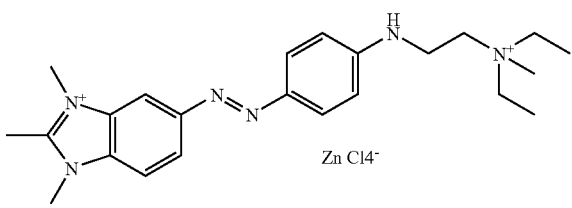

(2-{propyl[4-(1,2,3-trimethyl-1H-benzoimidazolium-5-ylazo)phenyl]amino}ethyl)trimethylammonium chlorozincate

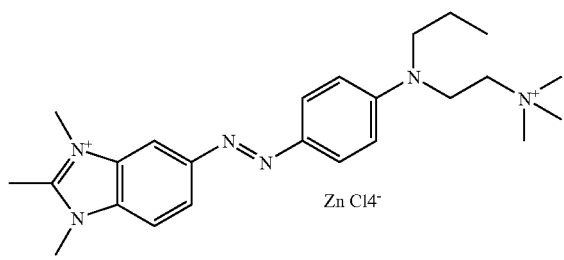

4-(2-{[4-(6-chloro-1,3-dimethyl-3H-benzoimidazolium-4-ylazo)phenyl]ethylamino}ethyl)-1-methylpyridinium tetrafluoroborate

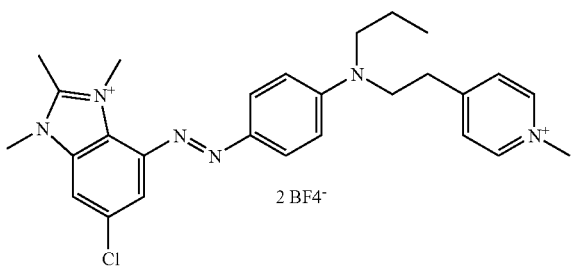

14

(2-{4-[5-(3-ethylbenzothiazolium-2-yl)-6-hydroxy-1-methyl-2-oxo-1,2-dihydropyridin-3-ylazo]phenyl}-2-oxoethyl)trimethylammonium methyl sulphate

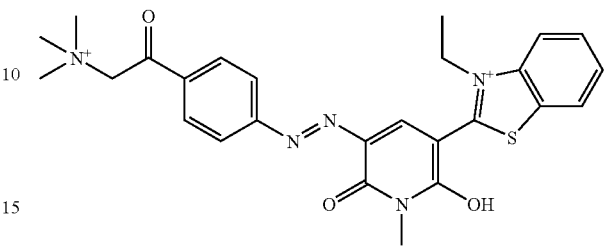

The composition according to the present patent application can comprise from 0.001 to 20%, preferably from 0.05 to 10% and more preferably still from 0.1 to 5% by weight of direct dye(s) of formula (I), with respect to the total weight of the composition.

The dyes of the invention can be prepared according to chemical reactions known per se starting from chromophores carrying a cationic charge which are capable of reacting with the nitrogenous hydrocarbon group chosen. The dyes can be prepared in particular by the process disclosed in the document U.S. Pat. No. 3,649,162.

The dyeing composition in accordance with the invention can additionally comprise one or more additional direct dyes other than the direct dyes of formula (I) described above which can be chosen from neutral, acidic or cationic nitrobenzene dyes, neutral, acidic or cationic azo direct dyes, neutral, acidic or cationic quinone and in particular anthraquinone direct dyes, azine direct dyes, triarylmethane direct dyes, indoamine direct dyes and natural direct dyes.

Mention may be made, as examples of additional direct dyes, of the cationic azo dyes disclosed in Patent Applications WO 95/15144, WO 95/01772 and EP 714 954.

Mention may very particularly be made, among these compounds, of the following dyes:
  1,3-dimethyl-2-[[4-(dimethylamino)phenyl]azo]-1H-imidazolium chloride,
  1,3-dimethyl-2-[(4-aminophenyl)azo]-1H-imidazolium chloride,
  1-methyl-4-[(methylphenylhydrazono)methyl]pyridinium methyl sulphate.

Mention may also be made, among additional azo direct dyes, of the following dyes, described in the Colour Index International, 3rd edition:
  Disperse Red 17
  Acid Yellow 9
  Acid Black 1
  Basic Red 22
  Basic Red 76
  Basic Yellow 57
  Basic Brown 16
  Acid Yellow 36
  Acid Orange 7
  Acid Red 33
  Acid Red 35
  Basic Brown 17
  Acid Yellow 23
  Acid Orange 24
  Disperse Black 9.

The additional direct dye or dyes preferably represent from 0.001 to 20% by weight approximately of the total weight of the ready-for-use composition and more preferably still from 0.005 to 10% by weight approximately.

By way of examples, the oxidation bases present in the compositions according to the invention are chosen from paraphenylenediamines, bisphenylalkylenediamines, para-aminophenols, ortho-aminophenols, heterocyclic bases, other than the heterocyclic para-phenylenediamines of formula (I), and their addition salts.

Mention may be made, among para-phenylenediamines, by way of examples, of para-phenylenediamine, para-toluylenediamine, 2-chloro-para-phenylenediamine, 2,3-dimethyl-para-phenylenediamine, 2,6-dimethyl-para-phenylenediamine, 2,6-diethyl-para-phenylenediamine, 2,5-dimethyl-para-phenylenediamine, N,N-dimethyl-para-phenylenediamine, N,N-diethyl-para-phenylenediamine, N,N-dipropyl-para-phenylenediamine, 4-amino-N,N-diethyl-3-methylaniline, N,N-bis(β-hydroxyethyl)-para-phenylenediamine, 4-N,N-bis(β-hydroxyethyl)amino-2-methylaniline, 4-N,N-bis(β-hydroxyethyl)amino-2-chloroaniline, 2-(β-hydroxyethyl)-para-phenylenediamine, 2-fluoro-para-phenylenediamine, 2-isopropyl-para-phenylenediamine, N-(β-hydroxypropyl)-para-phenylenediamine, 2-hydroxymethyl-para-phenylenediamine, N,N-dimethyl-3-methyl-para-phenylenediamine, N,N-(ethyl, β-hydroxyethyl)-para-phenylenediamine, N-(β,γ-dihydroxypropyl)-para-phenylenediamine, N-(4'-aminophenyl)-para-phenylenediamine, N-phenyl-para-phenylenediamine, 2-(β-hydroxyethyloxy)-para-phenylenediamine, 2-(β-acetylaminoethyloxy)-para-phenylenediamine, N-(β-methoxyethyl)-para-phenylenediamine, 4-aminophenylpyrrolidine, 2-thienyl-para-phenylenediamine, 2-(β-hydroxyethylamino)-5-aminotoluene, 3-hydroxy-1-(4'-aminophenyl)-pyrrolidine, and their addition salts with an acid.

Among the para-phenylenediamines mentioned above, para-phenylenediamine, para-toluylenediamine, 2-isopropyl-para-phenylenediamine, 2-(β-hydroxyethyl)-para-phenylenediamine, 2-(β-hydroxyethyloxy)-para-phenylenediamine, 2,6-dimethyl-para-phenylenediamine, 2,6-diethyl-paraphenylenediamine, 2,3-dimethyl-para-phenylenediamine, N,N-bis(β-hydroxyethyl)-para-phenylenediamine, 2-chloro-para-phenylenediamine, 2-(β-acetylaminoethyloxy)-para-phenylenediamine, and their addition salts with an acid, are particularly preferred.

Mention may be made, among bisphenylalkylenediamines, by way of examples, of N,N'-bis(β-hydroxyethyl)-N,N'-bis(4'-aminophenyl)-1,3-diaminopropanol, N,N'-bis(β-hydroxyethyl)-N,N'-bis(4-aminophenyl)ethylenediamine, N,N'-bis(4-aminophenyl)tetramethylenediamine, N,N'-bis(β-hydroxyethyl)-N,N'-bis(4-aminophenyl)tetramethylenediamine, N,N'-bis(4-methylaminophenyl)tetramethylenediamine, N,N'-bis(ethyl)-N,N'-bis(4'-amino-3'-methylphenyl)ethylenediamine, 1,8-bis(2,5-diaminophenoxy)-3,6-dioxaoctane, and their addition salts.

Mention may be made, among para-aminophenols, by way of examples, of para-aminophenol, 4-amino-3-methylphenol, 4-amino-3-fluorophenol, 4-amino-3-chlorophenol, 4-amino-3-(hydroxymethyl)phenol, 4-amino-2-methylphenol, 4-amino-2-(hydroxymethyl)phenol, 4-amino-2-(methoxymethyl)phenol, 4-amino-2-(aminomethyl)phenol, 4-amino-2-[(β-hydroxyethyl)aminomethyl]phenol, 4-amino-2-fluorophenol, and their addition salts with an acid.

Mention may be made, among ortho-aminophenols, by way of examples, of 2-aminophenol, 2-amino-5-methylphenol, 2-amino-6-methylphenol, 5-acetamido-2-aminophenol, and their addition salts.

Mention may be made, among heterocyclic bases, by way of examples, of pyridine derivatives, pyrimidine derivatives and pyrazole derivatives.

Mention may be made, among pyridine derivatives, of the compounds disclosed, for example, in Patents GB 1 026 978 and GB 1 153 196, such as 2,5-diaminopyridine, 2-(4-methoxyphenyl)amino-3-aminopyridine, 3,4-diaminopyridine, and their addition salts.

Other pyridine oxidation bases of use in the present invention are the oxidation bases 3-aminopyrazolo[1,5-a]pyridines or their addition salts disclosed, for example, in Patent Application FR 2 801 308. Mention may be made, by way of example, of pyrazolo[1,5-a]pyridin-3-ylamine; 2-(acetylamino)pyrazolo[1,5-a]-pyridin-3-ylamine; 2-(morpholin-4-yl)pyrazolo[1,5-a]-pyridin-3-ylamine; 3-aminopyrazolo[1,5-a]pyridine-2-carboxylic acid; 2-methoxypyrazolo[1,5-a]pyridin-3-ylamine; (3-aminopyrazolo[1,5-a]pyridin-7-yl)methanol; 2-(3-aminopyrazolo[1,5-a]pyridin-5-yl)ethanol; 2-(3-aminopyrazolo[1,5-a]pyridin-7-yl)ethanol; (3-aminopyrazolo[1,5-a]pyridin-2-yl)methanol; 3,6-diaminopyrazolo[1,5-a]pyridine; 3,4-diaminopyrazolo[1,5-a]-pyridine; pyrazolo[1,5-a]-pyridine-3,7-diamine; 7-(morpholin-4-yl)-pyrazolo[1,5-a]pyridin-3-ylamine; pyrazolo[1,5-a]-pyridine-3,5-diamine; 5-(morpholin-4-yl)-pyrazolo[1,5-a]pyridin-3-ylamine; 2-[(3-aminopyrazolo[1,5-a]pyridin-5-yl)(2-hydroxyethyl)amino]-ethanol; 2-[(3-aminopyrazolo[1,5-a]-pyridin-7-yl)(2-hydroxyethyl)amino]ethanol; 3-aminopyrazolo[1,5-a]-pyridin-5-ol; 3-aminopyrazolo[1,5-a]pyridin-4-ol; 3-aminopyrazolo[1,5-a]pyridin-6-ol; 3-aminopyrazolo[1,5-a]pyridin-7-ol; and their addition salts.

Mention may be made, among pyrimidine derivatives, of the compounds disclosed, for example, in Patents DE 2 359 399, JP 88-169 571, JP 05-63 124 or EP 0 770 375 or Patent Application WO 96/15765, such as 2,4,5,6-tetraaminopyrimidine, 4-hydroxy-2,5,6-triaminopyrimidine, 2-hydroxy-4,5,6-triaminopyrimidine, 2,4-dihydroxy-5,6-diaminopyrimidine, 2,5,6-triaminopyrimidine, and their addition salts and their tautomeric forms, when a tautomeric equilibrium exists.

Mention may be made, among pyrazole derivatives, of the compounds disclosed in Patents DE 3 843 892 and DE 4 133 957 and Patent Applications WO 94/08969, WO 94/08970, FR-A-2 733 749 and DE 195 43 988, such as 4,5-diamino-1-methylpyrazole, 4,5-diamino-1-(β-hydroxyethyl)pyrazole, 3,4-diaminopyrazole, 4,5-diamino-1-(4'-chlorobenzyl)pyrazole, 4,5-diamino-1,3-dimethylpyrazole, 4,5-diamino-3-methyl-1-phenylpyrazole, 4,5-diamino-1-methyl-3-phenylpyrazole, 4-amino-1,3-dimethyl-5-hydrazinopyrazole, 1-benzyl-4,5-diamino-3-methylpyrazole, 4,5-diamino-3-tert-butyl-1-methylpyrazole, 4,5-diamino-1-tert-butyl-3-methylpyrazole, 4,5-diamino-1-(β-hydroxyethyl)-3-methylpyrazole, 4,5-diamino-1-ethyl-3-methylpyrazole, 4,5-diamino-1-ethyl-3-(4'-methoxyphenyl)pyrazole, 4,5-diamino-1-ethyl-3-(hydroxymethyl)pyrazole, 4,5-diamino-3-hydroxymethyl-1-methylpyrazole, 4,5-diamino-3-hydroxymethyl-1-isopropylpyrazole, 4,5-diamino-3-methyl-1-isopropylpyrazole, 4-amino-5-(2'-aminoethyl)amino-1,3-dimethylpyrazole, 3,4,5-triaminopyrazole, 1-methyl-3,4,5-triaminopyrazole, 3,5-diamino-1-methyl-4-(methylamino)pyrazole, 3,5-diamino-4-(β-hydroxyethyl)amino-1-methylpyrazole, and their addition salts.

The oxidation base or bases present in the composition of the invention are generally present in an amount ranging from 0.001 to 20% by weight approximately of the total weight of the dyeing composition, preferably ranging from 0.005 to 6%.

The composition of the present invention can additionally comprise one or more oxidation dye precursors chosen from couplers.

The couplers can be chosen from the couplers conventionally used for the dyeing of keratinous fibres. Mention may in particular be made, among these couplers, of meta-phenylenediamines, meta-diphenols, naphthalene couplers, heterocyclic couplers and their addition salts.

Mention may be made, by way of examples, of 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-(dimethylamino)benzene, sesamol, 1-(β-hydroxyethylamino)-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)-toluene and their addition salts.

In the composition of the present invention, the coupler or couplers are generally present in an amount ranging from 0.001 to 20% by weight of the total weight of the dyeing composition, preferably ranging from 0.005 to 6%.

Generally, the addition salts of the oxidation bases and of the couplers which can be used in the context of the invention are chosen in particular from the addition salts with an acid, such as hydrochlorides, hydrobromides, sulphates, citrates, succinates, tartrates, lactates, tosylates, benzenesulphonates, phosphates and acetates, and the addition salts with a base, such as sodium hydroxide, potassium hydroxide, ammonia, amines or alkanolamines.

The medium appropriate for the dyeing, also referred to as dyeing vehicle, is a cosmetic medium generally composed of water or of a mixture of water and of at least one organic solvent, in order to dissolve the compounds which would be insufficiently soluble in water. Mention may be made, by way of organic solvent, for example, of lower $C_1$-$C_4$ alkanols, such as ethanol and isopropanol; polyols and polyol ethers, such as 2-butoxyethanol, propylene glycol, propylene glycol monomethyl ether, diethylene glycol monoethyl ether and diethylene glycol monomethyl ether, and also aromatic alcohols, such as benzyl alcohol or phenoxyethanol, and their mixtures.

The solvents are preferably present in proportions preferably of between 1 and 40% by weight approximately with respect to the total weight of the dyeing composition and more preferably still between 5 and 30% by weight approximately.

The dyeing composition in accordance with the invention can also include various adjuvants conventionally used in compositions for dyeing the hair, such as anionic, cationic, nonionic, amphoteric or zwitterionic surface-active agents or their mixtures, anionic, cationic, nonionic, amphoteric or zwitterionic polymers or their mixtures, inorganic or organic thickening agents and in particular anionic, cationic, nonionic and amphoteric polymeric associative thickeners, antioxidants, penetrating agents, sequestering agents, fragrances, buffers, dispersants, conditioning agents, such as, for example, volatile or nonvolatile and modified or unmodified silicones, film-forming agents, ceramides, preservatives or opacifiers.

The above adjuvants are generally present in an amount of, for each of them, between 0.01 and 20% by weight, with respect to the weight of the composition.

Of course, a person skilled in the art will take care to choose this or these optional additional compounds so that the advantageous properties intrinsically attached to the oxidation dyeing composition in accordance with the invention are not, or not substantially, detrimentally affected by the envisaged addition or additions.

The pH of the dyeing composition in accordance with the invention is generally between 3 and 12 approximately and preferably between 5 and 11 approximately. It can be adjusted to the desired value using acidifying or basifying agents generally used in dyeing keratinous fibres or else using conventional buffer systems.

Mention may be made, among acidifying agents, by way of examples, of inorganic or organic acids, such as hydrochloric acid, orthophosphoric acid, sulphuric acid, carboxylic acids, such as acetic acid, tartaric acid, citric acid or lactic acid, or sulphonic acids.

Mention may be made, among basifying agents, by way of examples, of ammonia, alkaline carbonates, alkanolamines, such as mono-, di- and triethanolamines, and their derivatives, sodium hydroxide, potassium hydroxide and the compounds of following formula (II):

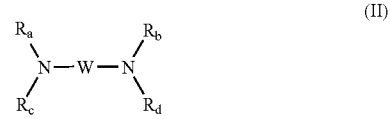

in which W is a propylene residue optionally substituted by a hydroxyl group or a $C_1$-$C_4$ alkyl radical and $R_a$, $R_b$, $R_c$ and $R_d$, which are identical or different, represent a hydrogen atom or a $C_1$-$C_4$ alkyl or $C_1$-$C_4$ hydroxyalkyl radical.

The dyeing composition according to the invention can be provided in various forms, such as in the form of liquids, creams or gels or in any other form appropriate for carrying out dyeing of keratinous fibres and in particular of human hair.

The implementation of the method according to the present patent application comprises the application of a dyeing composition according to the present patent application to keratinous fibres and then a stage which consists in leaving to stand for a period sufficient to make possible the colouring of the hair; this period is generally between 5 minutes and 1 hour and preferably between 15 minutes and 1 hour.

The method for dyeing keratinous fibres can comprise a stage in which use is made of an oxidizing agent at acidic, neutral or basic pH. The oxidizing agent can be added to the composition of the invention only at the moment of use or it can be employed starting from an oxidizing composition comprising it, applied simultaneously or sequentially with the composition of the invention.

This method can be employed in particular when the composition according to the invention comprises at least one oxidation dye precursor.

According to a particular embodiment, the composition according to the present invention comprising at least one oxidation dye precursor is mixed, preferably at the moment of use, with a composition comprising, in a medium appropriate for the dyeing, of at least one oxidizing agent, this oxidizing agent being present in an amount sufficient to develop a colouring. The mixture obtained is subsequently applied to keratinous fibres. After a leave-in time of 5 minutes to 1 hour approximately, preferably 15 minutes to 1 hour approximately, the keratinous fibres are rinsed, washed with shampoo, rinsed again and then dried.

The oxidizing agents conventionally used for the dyeing of keratinous fibres are, for example, hydrogen peroxide, urea peroxide, alkali metal bromates, persalts, such as perborates and persulphates, peracids and oxidase enzymes, among which may be mentioned peroxidases, 2-electron oxidoreductases, such as uricases, and 4-electron oxygenases, such as laccases. Hydrogen peroxide is particularly preferred.

The oxidizing composition can also include various adjuvants conventionally used in compositions for dyeing the hair and as defined above.

In the specific embodiment of the invention where the dyeing composition is mixed with an oxidizing composition, the pH of the oxidizing composition including the oxidizing agent is such that, after mixing with the dyeing composition, the pH of the resulting composition applied to the keratinous fibres preferably varies between 3 and 12 approximately and preferably between 5 and 11 approximately and more preferably still between 6 and 8.5. It can be adjusted to the desired value using acidifying or basifying pH-regulating agents commonly used in dyeing keratinous fibres and as defined above.

The composition applied to the keratinous fibres can be provided in various forms, such as in the form of liquids, creams or gels or in any other form appropriate for carrying out dyeing of keratinous fibres and in particular of human hair. In particular, it can be packaged under pressure in an aerosol container in the presence of a propellant and can form a foam.

Another subject-matter of the present patent application is a dyeing kit or multicompartment device in which a first compartment includes the dyeing composition defined above and a second compartment includes an oxidizing composition. This device can be equipped with a means which makes it possible to deliver the desired mixture over the hair, such as the devices disclosed in Patent FR 2 586 913 on behalf of the Applicant Company.

With this device, it is possible to dye keratinous fibres by a method which comprises the mixing of a dyeing composition in accordance with the invention with an oxidizing agent as defined above and the application of the mixture obtained to keratinous fibres for a time sufficient to develop the desired colouring.

The examples which follow are intended to illustrate the invention without, however, exhibiting a limiting nature.

EXAMPLE 1

| Dyeing composition for dyeing hair blue | |
|---|---|
| Dye (1) | 0.15 g |
| Ethanol | 10 g |
| Alkyl polyglucoside | 5 g of active material |
| 2-Amino-2-methylpropanol | q.s. for pH 8.0 |
| Water   q.s. for | 100 g |

(1) 2-[[4-[ethyl[2-(trimethylammonio)ethyl]amino]-phenyl]azo]-4-(methoxycarbonyl)-5-(2-methoxy-2-oxo-ethyl)-3-methylthiazolium

EXAMPLE 2

| Dyeing composition for dyeing hair red | |
|---|---|
| Dye (1) | 0.15 g |
| Ethanol | 10 g |
| Alkyl polyglucoside | 5 g of active material |
| 2-Amino-2-methylpropanol | q.s. for pH 8.0 |
| Water   q.s. for | 100 g |

(1) 2-[[4-[[2-(diethylmethylammonio)ethyl]ethylamino]-2-methylphenyl]azo]-1,3-dimethyl-1H-imidazolium diiodide

EXAMPLE 3

| Dyeing composition for dyeing hair blue | |
|---|---|
| Dye (1) | 0.15 g |
| Ethanol | 10 g |
| Alkyl polyglucoside | 5 g of active material |
| 2-Amino-2-methylpropanol | q.s. for pH 8.0 |
| Water   q.s. for | 100 g |

(1) 2-[[4-[ethyl[2-(trimethylammonio)ethyl]amino]-phenyl]azo]-6-methoxy-3-methylbenzothiazolium sulphate

The invention claimed is:

1. A dyeing composition for dyeing keratinous fibres, comprising, in an appropriate dyeing medium, at least one oxidation base and at least one direct dye of formula (I):

$$A-N=N-B-L-\overset{R2}{\underset{R3}{N^+}}-R1 \quad zXz'-$$
(I)

wherein:
Xz'− is chosen from organic and inorganic anions;
z and z' are such that the overall charge of the molecule is zero;
A is a positively-charged heterocyclic ring chosen from:
  substituted and unsubstituted thiazolium, wherein the thiazolium is substituted with at most one alkoxycarbonyl functional group;
  substituted and unsubstituted imidazolium;
  substituted and unsubstituted benzimidazolium;
  substituted and unsubstituted benzothiazolium pyridino;
  substituted and unsubstituted naphthothiazolium; and
  substituted benzothiazolium;
B is chosen from optionally substituted $C_6$-$C_{30}$ arylene groups and optionally substituted 5- to 10-membered heterocyclic groups;
L is chosen from substituted and unsubstituted, linear, branched, and cyclic $C_1$-$C_{30}$ alkylene radicals,
  wherein the $C_1$-$C_{30}$ alkylene radicals are optionally interrupted or terminated by at least one heteroatomic group chosen from O, S, NH or NR, wherein R is chosen from linear and branched $C_1$-$C_{10}$ alkyl radicals,
  wherein the $C_1$-$C_{30}$ alkylene radicals are optionally interrupted by at least one radical chosen from heterocyclic and nonheterocyclic, aromatic and nonaromatic, cyclic radicals, and
wherein the $C_1$-$C_{30}$ alkylene radicals optionally carry at least one quaternary cationic charge, and wherein at least one carbon atom of the $C_1$-$C_{30}$ alkylene radical is optionally replaced by a carbonyl group;

R1, R2 and R3 are independently chosen from:
  optionally substituted, linear, branched and cyclic $C_1$-$C_{10}$ alkyl radicals;
  optionally substituted, linear, branched and cyclic $C_1$-$C_{10}$ arylalkyl radicals;
  optionally substituted aryl radicals; and
  linear and branched $C_1$-$C_{10}$ aryloxyalkyl radicals;
wherein at least one of the R1, R2, and R3 radicals may form, with the nitrogen atom carrying it, and optionally with L, an optionally substituted, saturated or unsaturated, 5- to 10-membered heterocycle that optionally comprises at least one additional heteroatom.

2. The dyeing composition according to claim 1, wherein the keratinous fibres are human keratinous fibres.

3. The dyeing composition according to claim 2, wherein the human keratinous fibres are human hair.

4. The dyeing composition according to claim 1, wherein the at least one direct dye of formula (I) is chosen from:
  2-[[4-ethyl[2-trimethylammonio)ethyl]amino]phenyl]azo]-4-(methoxycarbonyl)-5-(2-methoxy-2-oxoethyl)-3-methylthiazolium;
  2-[[4-[[2-[dimethyl(phenylmethyl)ammonio]ethyl]ethylamino]phenyl]azo-3-methylthiazolium dichloride;
  2-[[4-(diethylamino)-2-[[trimethylammonio)acetyl]amino]phenyl]azo]-5-(ethoxycarbonyl)-3-methyl-4-phenylthiazolium;
  2-[[4-(diethylamino)-2-[[(trimethylammonio)acetyl]oxy]phenyl]azo]-5-(ethoxycarbonyl)-3,4-dimethylthiazolium bis[tetrafluoroborate(1-)];
  2-[[4-(diethylamino)-2-[[(trimethylammonio)acetyl]oxy]phenyl]azo]-5-(ethoxycarbonyl)-3,4-dimethylthiazolium;
  2-[[4-ethyl[2-[(2-hydroxypropyl)dimethylammonio]ethyl]amino]-2-methylphenyl]azo]-3-methylthiazolium dichloride;
  2-[[4-[ethyl(2-(trimethylammonio)ethyl]amino]phenyl]azo]-3-methylthiazolium dichloride;
  2-[[4-[ethyl[2-(trimethylammonio)ethyl]amino]phenyl]azo]-3-methyl-4-phenylthiazolium bis[tetrafluoroborate(1-)];
  2-[[4-[ethyl[2-(trimethylammonio)ethyl]amino]phenyl]azo]-3-methyl-4-phenylthiazolium;
  1-(2-{(4-methoxyphenyl)-[3-methyl-4-(thiazol-3-ium-2-ylazo)phenyl]amino}ethyl)-4-methylpyridinium chloride;
  1-(2-{phenyl-[5-ethoxycarbonyl-3,4-dimethyl-4-(thiazol-3-ium-2-ylazo)phenyl]amino}ethyl)pyridinium chlorozincate;
  1-(2-{(4-methoxyphenyl)[5-ethoxycarbonyl-3,4-dimethyl-4-(thiazol-3-ium-2-ylazo)phenyl]amino}ethyl)-4-methylpyridinium chloride;
  4-dimethylamino-1-(2-{[4-(5-ethoxycarbonyl-3,4-dimethyl-4-(thiazol-3-ium-2-ylazo)phenyl](p-tolyl)amino}ethyl)pyridinium chlorozincate;
  1-{2-[[4-(5-acetyl-3,4-dimethyl-4-(thiazol-3-ium-2-ylazo)phenyl](4-methoxyphenyl)amino]ethyl}pyridinium chloride;
  1-(3-{[4-(5-ethoxycarbonyl-3,4-dimethyl-4-(thiazol-3-ium-2-ylazo)phenyl](phenyl)amino}-2-hydroxypropyl)-pyridinium chlorozincate;
  1-{3-[[4-(5-ethoxycarbonyl-3,4-dimethyl-4-(thiazol-3-ium-2-ylazo)phenyl](4-methoxyphenyl)amino]-2-hydroxypropyl}-4-methylpyridinium chloride;
  4-[4-[((1,3-dimethyl-1H-imidazolium-2-yl)azo]phenyl]-1,1-dimethylpiperazinium diiodide;
  2-[[4-[ethyl[2-[[(trimethylammonio)acetyl]amino]ethyl]amino]-2-methylphenyl]azo]-1,3-dimethyl-1H-imidazolium diiodide;
  2-[[4-[[3-(diethylmethylammonio)-2-hydroxypropyl]ethylamino]-2-methylphenyl]azo]-1,3-dimethyl-1H-imidazolium diiodide;
  2-[[4-[[2-(diethylmethylammonio)ethyl]ethylamino]-2-methylphenyl]azo]-1,3-dimethyl-1H-imidazolium diiodide;
  2-[[4-[ethyl2-(trimethylammonio)ethyl]amino]phenyl]azo]-1,3-dimethyl-1H-imidazolium diiodide;
  2-[[4-[[2-(diethylmethylammonio)ethyl]ethylamino]-phenyl]azo]-1,3-dimethyl-1H-imidazolium diiodide;
  2-[[4-[ethyl[2-(trimethylammonio)ethyl]amino]phenyl]azo]-3-methylnapththo[2,1-d]thiazolium dichloride;
  2-[[4-anilino-2-(ethylamino)-6-[[3-(trimethylammonio)propyl]amino]-5-pyrimidinyl]azo]-6-methoxy-3-methyl benzothiazolium bis(methylsulphate);
  2-[[2-(ethylamino)-4-(phenylamino)-6-[[3-(trimethylammonio)propyl]amino]-5-pyrimidinyl]azo]-6-methoxy-3-methylbenzothiazolium;
  2-[[4-[ethyl[2-(trimethylammonio)ethyl]amino]phenyl]azo]-6-methoxy-3-methylbenzothiazolium sulphate;
  2-[[4-[ethyl[2-(trimethylammonio)ethyl]amino]phenyl]azo]-6-methoxy-3-methylbenzothiazolium diacetate;
  2-[[4-[ethyl[2-(trimethylammonio)ethyl]amino]phenyl]azo]-6-methoxy-3-methylbenzothiazolium bis(methylsulphate);
  2-[[4-[ethyl[2-(trimethylammonio)ethyl]amino]phenyl]azo]-6-methoxy-3-methylbenzothiazolium;
  6-ethoxy-2-[[4-[ethyl[2-hydroxy-3-(trimethylammonio)propyl]amino]-2-methylphenyl]azo]-3-methylbenzothiazolium bis[tetrafluoroborate(1-)];
  6-ethoxy-2-[[4-[ethyl[2-hydroxy-3-(trimethylammonio)propyl]amino]-2-methylphenyl]azo]-3-methylbenzothiazolium;
  3-[4-(6-methoxy-3-methylbenzothiazol-3-ium)phenyl]-3-aza-6-azoniaspiro[5.5]undecane dichloride;
  diethyl(2-{ethyl[4-(3-methylbenzothiazol-2-ylazo)phenyl]amino}ethyl)(2-phenoxyethyl)ammonium dichloride;
  1-(2-{ethyl[4-(6-methoxy-3-methylbenzothiazolium-2-ylazo)phenyl]amino}ethyl)pyridinium tetrafluoroborate;
  (2-{ethyl[4-(1,2,3-trimethyl-1H-benzoimidazolium-5-ylazo)phenyl]amino}ethyl)trimethylammonium chlorozincate;
  diethylmethyl{2-[3-methyl[4-(1,2,3-trimethyl-1H-benzoimidazolium-5-ylazo)phenylamino]ethyl}ammonium chlorozincate;
  (2-{propyl[4-(1,2,3-trimethyl-1H-benzoimidazolium-5-ylazo)phenyl]amino}ethyl)trimethylammonium chlorozincate;
  4-(2-{[4-(6-chloro-1,3-dimethyl-3H-benzoimidazolium-4-ylazo)phenyl]ethylamino}ethyl)-1-methylpyridinium tetrafluoroborate; and
  (2-{4-[5-(3-ethylbenzothiazolium-2-yl)-6-hydroxy-1-methyl-2-oxo-1,2-dihydropyridin-3-ylazo]phenyl}-2-oxoethyl)trimethylammonium methyl sulphate.

5. The dyeing composition according to claim 1, wherein the at least one direct dye of formula (I) is present in an amount ranging from 0.001% to 20% by weight, with respect to the total weight of the composition.

6. The dyeing composition according to claim 5, wherein the at least one direct dye of formula (I) is present in an amount ranging from 0.1% to 5% by weight, with respect to the total weight of the composition.

7. The dyeing composition according to claim 1, wherein the at least one oxidation base is chosen from para-phenylenediamines, bisphenylalkylenediamines, para-aminophenols, ortho-aminophenols, heterocyclic bases, and addition salts thereof.

8. The dyeing composition according to claim 1, wherein the at least one oxidation base is present in an amount ranging from 0.001% to 20% by weight, relative to the total weight of the composition.

9. The dyeing composition according to claim 8, wherein the at least one oxidation base is present in an amount ranging from 0.005% to 6% by weight, relative to the total weight of the composition.

10. The dyeing composition according to claim 1, further comprising at least one additional direct dye.

11. The dyeing composition according to claim 1, further comprising at least one oxidation dye precursor chosen from couplers.

12. The dyeing composition according to claim 11, wherein the at least one coupler is chosen from meta-phenylenediamines, meta-aminophenols, meta-diphenols, naphthalene couplers, heterocyclic couplers, and addition salts thereof.

13. The dyeing composition according to claim 12, wherein the at least one coupler is chosen from 1,3-dihydroxybenzene, 1,3-dihydroxy-2-methylbenzene, 4-chloro-1,3-dihydroxybenzene, 2,4-diamino-1-(β-hydroxyethyloxy)benzene, 2-amino-4-(β-hydroxyethylamino)-1-methoxybenzene, 1,3-diaminobenzene, 1,3-bis(2,4-diaminophenoxy)propane, 3-ureidoaniline, 3-ureido-1-(dimethylamino)benzene, sesamol, 1-(β-hydroxyethylamino)-3,4-methylenedioxybenzene, α-naphthol, 2-methyl-1-naphthol, 6-hydroxyindole, 4-hydroxyindole, 4-hydroxy-N-methylindole, 2-amino-3-hydroxypyridine, 6-hydroxybenzomorpholine, 3,5-diamino-2,6-dimethoxypyridine, 1-N-(β-hydroxyethyl)amino-3,4-methylenedioxybenzene, 2,6-bis(β-hydroxyethylamino)toluene, and addition salts thereof.

14. The dyeing composition according to claim 11, wherein the at least one coupler is present in an amount ranging from 0.001% to 20% by weight, relative to the total weight of the composition.

15. The dyeing composition according to claim 14, wherein the at least one coupler is present in an amount ranging from 0.005% to 6% by weight, relative to the total weight of the composition.

16. The dyeing composition according to claim 1, further comprising at least one solvent.

17. The dyeing composition according to claim 16, wherein the at least one solvent is chosen from ethanol, propylene glycol, glycerol, and polyol monoethers.

18. The dyeing composition according to claim 1, further comprising at least one adjuvant chosen from anionic, cationic, nonionic, amphoteric, and zwitterionic surfactants; anionic, cationic, nonionic, amphoteric, and zwitterionic polymers; inorganic thickening agents; organic thickening agents; antioxidants; penetrating agents; sequestering agents; fragrances; buffers; dispersants; conditioning agents; film-forming agents; ceramides; preservatives; and opacifiers.

19. The dyeing composition according to claim 1, further comprising at least one oxidizing agent chosen from hydrogen peroxide, urea peroxide, alkali metal bromates, persalts, peracids, and oxidase enzymes.

20. The dyeing composition according to claim 19, wherein the at least one oxidizing agent is hydrogen peroxide.

21. A process for dyeing keratinous fibres, comprising applying to the keratinous fibres a dyeing composition comprising, in an appropriate dyeing medium, at least one oxidation base and at least one direct dye of formula (I):

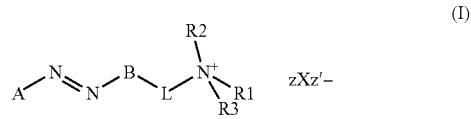

wherein:
Xz'− is chosen from organic and inorganic anions;
z and z' are such that the overall charge of the molecule is zero;
A is a positively-charged heterocyclic ring chosen from:
  substituted and unsubstituted thiazolium, wherein the thiazolium is substituted with at most one alkoxycarbonyl functional group;
  substituted and unsubstituted imidazolium;
  substituted and unsubstituted benzimidazolium;
  substituted and unsubstituted benzothiazolium pyridino;
  substituted and unsubstituted naphthothiazolium; and
  substituted benzothiazolium;
B is chosen from optionally substituted $C_6$-$C_{30}$ arylene groups and optionally substituted 5- to 10-membered heterocyclic groups;
L is chosen from substituted and unsubstituted, linear, branched, and cyclic $C_1$-$C_{30}$ alkylene radicals,
  wherein the $C_1$-$C_{30}$ alkylene radicals are optionally interrupted or terminated by at least one heteroatomic group chosen from O, S, NH or NR, wherein R is chosen from linear and branched $C_1$-$C_{10}$ alkyl radicals,
  wherein the $C_1$-$C_{30}$ alkylene radicals are optionally interrupted by at least one radical chosen from heterocyclic and nonheterocyclic, aromatic and non-aromatic, cyclic radicals, and
  wherein the $C_1$-$C_{30}$ alkylene radicals optionally carry at least one quaternary cationic charge, and wherein at least one carbon atom of the $C_1$-$C_{30}$ alkylene radical is optionally replaced by a carbonyl group;
R1, R2 and R3 are independently chosen from:
  optionally substituted, linear, branched and cyclic $C_1$-$C_{10}$ alkyl radicals
  optionally substituted, linear, branched and cyclic $C_1$-$C_{10}$ arylalkyl radicals;
  optionally substituted aryl radicals; and
  linear and branched $C_1$-$C_{10}$ aryloxyalkyl radicals;
wherein at least one of the R1, R2, and R3 radicals may form, with the nitrogen atom carrying it, and optionally with L, an optionally substituted, saturated or unsaturated, 5- to 10-membered heterocycle that optionally comprises at least one additional heteroatom; and
  leaving the dyeing composition on the fibers for a period of time ranging from 5 minutes to 1 hour.

22. The process of claim 21, wherein the dyeing composition is left to stand for a period of time ranging from 15 minutes to 1 hour.

23. The process of claim 21, wherein the keratinous fibres are human keratinous fibres.

24. The process of claim 23, wherein the human keratinous fibres are human hair.

25. A method of obtaining hair colourings that are substantially resistant to external agents and to shampooing operations, comprising
applying to the keratinous fibres a dyeing composition comprising, in an appropriate dyeing medium, at least one oxidation base and at least one direct dye of formula (I):

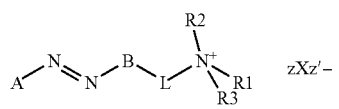

(I)

wherein:
Xz'$^-$ is chosen from organic and inorganic anions;
z and z' are such that the overall charge of the molecule is zero;
A is a positively-charged heterocyclic ring chosen from:
substituted and unsubstituted thiazolium, wherein the thiazolium is substituted with at most one alkoxycarbonyl functional group;
substituted and unsubstituted imidazolium;
substituted and unsubstituted benzimidazolium;
substituted and unsubstituted benzothiazolium pyridino;
substituted and unsubstituted naphthothiazolium; and
substituted benzothiazolium;
B is chosen from optionally substituted $C_6$-$C_{30}$ arylene groups and optionally substituted 5- to 10-membered heterocyclic groups;
L is chosen from substituted and unsubstituted, linear, branched, and cyclic $C_1$-$C_{30}$ alkylene radicals,
wherein the $C_1$-$C_{30}$ alkylene radicals are optionally interrupted or terminated by at least one heteroatomic group chosen from O, S, NH or NR, wherein R is chosen from linear and branched $C_1$-$C_{10}$ alkyl radicals,
wherein the $C_1$-$C_{30}$ alkylene radicals are optionally interrupted by at least one radical chosen from heterocyclic and nonheterocyclic, aromatic and non-aromatic, cyclic radicals, and
wherein the $C_1$-$C_{30}$ alkylene radicals optionally carry at least one quaternary cationic charge, and wherein at least one carbon atom of the $C_1$-$C_{30}$ alkylene radical is optionally replaced by a carbonyl group;
R1, R2 and R3 are independently chosen from:
optionally substituted, linear, branched and cyclic $C_1$-$C_{10}$ alkyl radicals
optionally substituted, linear, branched and cyclic $C_1$-$C_{10}$ arylalkyl radicals;
optionally substituted aryl radicals; and
linear and branched $C_1$-$C_{10}$ aryloxyalkyl radicals;
wherein at least one of the R1, R2, and R3 radicals may form, with the nitrogen atom carrying it, and optionally with L, an optionally substituted, saturated or unsaturated, 5- to 10-membered heterocycle that optionally comprises at least one additional heteroatom.

26. The method of claim 25, wherein the keratinous fibres are human keratinous fibres.

27. The method of claim 26, wherein the human keratinous fibres are human hair.

28. A method of manufacturing a dyeing composition for keratinous fibres, comprising adding to a cosmetically acceptable medium at least one direct dye of formula (I):

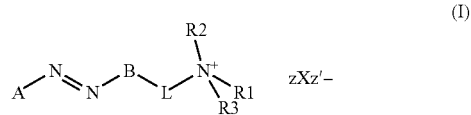

(I)

wherein:
Xz'$^-$ is chosen from organic and inorganic anions;
z and z' are such that the overall charge of the molecule is zero;
A is a positively-charged heterocyclic ring chosen from:
substituted and unsubstituted thiazolium, wherein the thiazolium is substituted with at most one alkoxycarbonyl functional group;
substituted and unsubstituted imidazolium;
substituted and unsubstituted benzimidazolium;
substituted and unsubstituted benzothiazolium pyridino;
substituted and unsubstituted naphthothiazolium; and
substituted benzothiazolium;
B is chosen from optionally substituted $C_6$-$C_{30}$ arylene groups and optionally substituted 5- to 10-membered heterocyclic groups;
L is chosen from substituted and unsubstituted, linear, branched, and cyclic $C_1$-$C_{30}$ alkylene radicals,
wherein the $C_1$-$C_{30}$ alkylene radicals are optionally interrupted or terminated by at least one heteroatomic group chosen from O, S, NH or NR, wherein R is chosen from linear and branched $C_1$-$C_{10}$ alkyl radicals,
wherein the $C_1$-$C_{30}$ alkylene radicals are optionally interrupted by at least one radical chosen from heterocyclic and nonheterocyclic, aromatic and non-aromatic, cyclic radicals, and
wherein the $C_1$-$C_{30}$ alkylene radicals optionally carry at least one quaternary cationic charge, and wherein at least one carbon atom of the $C_1$-$C_{30}$ alkylene radical is optionally replaced by a carbonyl group;
R1, R2 and R3 are independently chosen from:
optionally substituted, linear, branched and cyclic $C_1$-$C_{10}$ alkyl radicals
optionally substituted, linear, branched and cyclic $C_1$-$C_{10}$ arylalkyl radicals;
optionally substituted aryl radicals; and
linear and branched $C_1$-$C_{10}$ aryloxyalkyl radicals;
wherein at least one of the R1, R2, and R3 radicals may form, with the nitrogen atom carrying it, and optionally with L, an optionally substituted, saturated or unsaturated, 5- to 10-membered heterocycle that optionally comprises at least one additional heteroatom.

* * * * *